(12) United States Patent
Organ et al.

(10) Patent No.: US 9,579,625 B2
(45) Date of Patent: Feb. 28, 2017

(54) FLUID PROCESSING APPARATUS

(71) Applicant: TOTAL SYNTHESIS LTD., Toronto (CA)

(72) Inventors: Michael Organ, Burlington (CA); Debasis Mallik, Newmarket (CA)

(73) Assignee: Total Synthesis Ltd., Toronto, Ontario (CA)

( * ) Notice: Subject to any disclaimer, the term of this patent is extended or adjusted under 35 U.S.C. 154(b) by 510 days.

(21) Appl. No.: 14/032,575

(22) Filed: Sep. 20, 2013

(65) Prior Publication Data
US 2014/0087036 A1    Mar. 27, 2014

Related U.S. Application Data

(60) Provisional application No. 61/703,822, filed on Sep. 21, 2012.

(51) Int. Cl.
| | |
|---|---|
| *H05B 6/80* | (2006.01) |
| *H05B 6/72* | (2006.01) |
| *B01J 19/00* | (2006.01) |
| *A61L 2/12* | (2006.01) |
| *B01J 19/12* | (2006.01) |
| *G01N 35/10* | (2006.01) |
| *G01N 1/44* | (2006.01) |
| *A23L 3/01* | (2006.01) |

(52) U.S. Cl.
CPC .............. *B01J 19/126* (2013.01); *A23L 3/01* (2013.01); *B01J 19/0093* (2013.01); *G01N 1/44* (2013.01); *G01N 35/1097* (2013.01); *B01J 2219/00792* (2013.01); *B01J 2219/00824* (2013.01); *B01J 2219/00831* (2013.01); *B01J 2219/00873* (2013.01); *B01J 2219/00941* (2013.01); *B01J 2219/00963* (2013.01); *B01J 2219/00986* (2013.01)

(58) Field of Classification Search
CPC .................. B01J 19/0093; B01J 19/126; B01J 2219/00792; B01J 2219/00824; B01J 2219/00831; B01J 2219/00873; B01J 2219/00941; B01J 2219/00963; B01J 2219/00986; G01N 35/1097; G01N 1/44; A23L 3/01
USPC .. 219/687, 688, 689, 686, 643, 635; 422/21, 106, 129, 130, 186, 208, 242, 307, 422/905; 423/659
See application file for complete search history.

(56) References Cited

U.S. PATENT DOCUMENTS

| | | |
|---|---|---|
| 3,213,669 A | 10/1965 | Taft et al. |
| 3,939,406 A | 2/1976 | Billeter et al. |
| 4,271,697 A | 6/1981 | Mowery, Jr. |
| 4,478,095 A | 10/1984 | Bradley et al. |

(Continued)

*Primary Examiner* — Quang Van
(74) *Attorney, Agent, or Firm* — Bereskin & Parr LLP/S.E.N.C.R.L., s.r.l.; James Raakman; Adrienne Bieber McNeil

(57) ABSTRACT

A fluid processing assembly includes a lumen for receiving at least one inlet stream and dispensing a primary product stream, and an energizing device for supplying energy to an energizable portion of the lumen. A primary product collection assembly is in fluid communication with the lumen for receiving the primary product stream. The energizable portion is positioned exterior to the primary product collection assembly. A pressurized gas source is downstream of the lumen. The pressurized gas source supplies pressurized gas to the primary product collection assembly for pressurizing at least a portion of the primary product collection assembly and the lumen.

21 Claims, 13 Drawing Sheets

(56) References Cited

U.S. PATENT DOCUMENTS

| | | |
|---|---|---|
| 4,645,647 A | 2/1987 | Yoshida et al. |
| 4,678,639 A | 7/1987 | Dong et al. |
| 4,713,974 A | 12/1987 | Stone |
| 4,816,226 A | 3/1989 | Jordan et al. |
| 4,930,898 A | 6/1990 | Miller-Ihli |
| 4,975,246 A | 12/1990 | Charm |
| 5,114,667 A | 5/1992 | Hayashi et al. |
| 5,215,715 A | 6/1993 | Haswell et al. |
| 5,382,414 A | 1/1995 | Lautenschlager |
| 5,389,335 A | 2/1995 | Charm et al. |
| 5,420,039 A | 5/1995 | Renoe et al. |
| 5,672,316 A | 9/1997 | Knapp |
| 5,814,742 A | 9/1998 | Vissers et al. |
| 6,143,573 A | 11/2000 | Rao et al. |
| 6,203,760 B1 | 3/2001 | van der Plaats et al. |
| 6,569,672 B1 | 5/2003 | Laugharn, Jr. et al. |
| 6,706,245 B2 | 3/2004 | Neal et al. |
| 6,740,858 B2 | 5/2004 | Tracy et al. |
| 6,863,805 B1 * | 3/2005 | Barreras, Sr. ........ B01D 21/302 210/143 |
| 6,976,383 B2 | 12/2005 | Petro et al. |
| 7,178,414 B1 | 2/2007 | Kokosa |
| 7,214,913 B2 | 5/2007 | Collins, Jr. et al. |
| 7,700,046 B2 | 4/2010 | Goldenberg |
| 2001/0031932 A1 | 10/2001 | Blake et al. |
| 2003/0091487 A1 | 5/2003 | Fagrell |
| 2003/0198578 A1 | 10/2003 | Lee et al. |
| 2004/0155034 A1 | 8/2004 | Feher et al. |
| 2005/0019216 A1 | 1/2005 | Trutnau |
| 2005/0045625 A1 | 3/2005 | Collins, Jr. et al. |
| 2005/0123970 A1 | 6/2005 | Ozbal et al. |
| 2005/0217393 A1 | 10/2005 | Tomita et al. |
| 2007/0212267 A1 | 9/2007 | Organ et al. |
| 2008/0134804 A1 | 6/2008 | Maeda et al. |
| 2009/0142845 A1 | 6/2009 | Benali et al. |
| 2009/0145205 A1 | 6/2009 | Hochgraeber et al. |
| 2010/0059428 A1 | 3/2010 | Boren et al. |
| 2010/0065512 A1 | 3/2010 | Bjorsvik |
| 2010/0077874 A1 * | 4/2010 | Kanomata ......... B01D 11/0203 73/863.21 |
| 2010/0264015 A1 | 10/2010 | Portnoff et al. |
| 2011/0189056 A1 | 8/2011 | Brownell et al. |

\* cited by examiner

FLUID PROCESSING APPARATUS

CROSS REFERENCE TO RELATED APPLICATION(S)

This application claims the benefit of 35 USC 119 based on the priority of U.S. Provisional Patent Application 61/703,822, filed Sep. 21, 2012, this application being incorporated herein in its entirety by reference.

FIELD

The disclosure relates to fluid processing apparatuses, such as microwave reactor apparatuses. More specifically, the disclosure relates to fluid processing apparatuses which may be operated under pressure, and to methods and devices for removing samples from such apparatuses, for withdrawing products from such apparatuses, and for analyzing samples from such apparatuses.

BACKGROUND

U.S. Patent Application Publication No. 2007/0212267 (Organ et al.) purports to disclose a reactor apparatus including at least one reaction capillary having a lumen for receiving a reactant to undergo a reaction, and a magnetron for irradiating reactant contained in at least a portion of the capillary with microwaves. This patent further purports to disclose a method of micro-reacting a reactant including providing a capillary, and irradiating the reactant in the capillary with microwaves to facilitate a chemical reaction in the capillary by which the reactant is converted into a desired product.

U.S. Pat. No. 5,672,316 (Knapp) purports to disclose a microwave-heatable pressure reactor for continuous or discontinuous treatment of liquid. The liquid is conveyed by means of a high-pressure pump in a pipeline which extends into a microwave-heatable zone of the pressure container into which it finally lets out through the free opening with a volume of pipe sufficient for the treatment of a desired quantity of liquid.

U.S. Pat. No. 7,178,414 (Kokosa) purports to disclose a method and apparatus for automatically performing liquid microextraction on liquid samples. The method includes the steps of controlling movement of a syringe between a cleaning station, a sample station containing a plurality of discrete sample vials and an instrument injector station. Movement of the syringe is controlled automatically for cleaning the syringe, obtaining a sample of each sample in each discrete sample vial, one at a time, and injecting the collected sample into the instrument injector, and then repeating the sequence steps for all discreet samples.

SUMMARY

The following summary is intended to introduce the reader to various aspects of the applicant's teaching, but not to define any invention.

According to one aspect, a fluid processing assembly comprises a lumen for receiving at least one inlet stream and dispensing a primary product stream, and an energizing device for supplying energy to an energizable portion of the lumen. A primary product collection assembly is in fluid communication with the lumen for receiving the primary product stream. The energizable portion is positioned exterior to the primary product collection assembly. A pressurized gas source is downstream of the lumen. The pressurized gas source supplies pressurized gas to the primary product collection assembly for pressurizing at least a portion of the primary product collection assembly and the lumen.

In some examples, the fluid processing assembly may further comprise a tube, and the tube may form the lumen.

In some examples, the energizing device may comprise an irradiating device irradiating an irradiation zone. The energizable portion may be within the irradiation zone. The irradiating device may comprise a microwave irradiating device. The primary product collection assembly may comprise a product collection vessel that is non-transparent to microwaves.

In some examples, the fluid processing assembly may comprise a valve downstream of the lumen and upstream of the primary product collection assembly. The valve may be movable to divert a sample of the primary product stream away from the primary product collection assembly. The valve may be configured to divert the sample without effectively de-pressurizing the portion of the primary product collection assembly and the lumen. The valve may be a multi-port multi-position valve, which may be movable to direct the primary product stream from the lumen to the primary product collection assembly, isolate a plug from product stream, and divert the plug to a sample stream.

According to another aspect, a method for processing fluids comprises a) supplying a pressurized gas to a primary product collection assembly to pressurize at least a portion of the primary product collection assembly and a lumen upstream of the primary product collection assembly; b) flowing at least one inlet stream into the lumen; c) supplying energy to an energizable portion of the lumen, the energizable portion positioned exterior to the primary product collection assembly; and d) dispensing a primary product stream from the lumen into the portion of the primary product collection assembly.

In some examples, step c) may comprise irradiating the energizable portion with microwaves.

In some examples, the method may further comprise e) diverting a sample of the primary product stream away from the primary product collection assembly while maintaining the pressure in the primary product collection assembly and in the lumen. Step e) may comprise moving a multi-port multi-position valve to isolate a plug from the primary product stream, and divert the plug to a sample stream.

According to another aspect, a fluid processing assembly comprises a pressurized lumen for receiving at least one inlet stream and dispensing a primary product stream, an energizing device for supplying energy to an energizable portion of the lumen, and a primary product collection assembly. The primary product collection assembly has at least a portion that is pressurized and in fluid communication with the lumen for receiving the product stream. A valve is downstream of the lumen and upstream of the primary product collection assembly. The valve is movable to divert a sample of the primary product stream away from the portion of the primary product collection assembly while maintaining the pressure in the portion of the product collection vessel and the lumen.

In some examples, the valve may be a multi-port multi-position valve. The multi-port multi-position valve may be a 6-port 2-position valve.

In some examples, the valve may be movable to direct the primary product stream to the portion of the primary product collection vessel, isolate a plug from the primary product stream, and divert the plug to a sample stream.

In some examples, the fluid processing assembly may further comprise a sample collection vessel in communication with the sample stream for receiving the plug from the sample stream.

In some examples, the fluid processing assembly may further comprise a solvent stream connected to the valve. The valve may be movable to direct the solvent stream into the sample stream.

In some examples, the valve may be positionable in a first position wherein the primary product stream is directed to the primary product collection vessel, and the solvent stream is directed into the sample stream. The valve may be movable from the first position to at least a second position. When in the second position, the plug of the product stream may be collected. The valve may be movable from the second position back to the first position, and when the valve is moved back to the first position from the second position, the plug may be isolated from the primary product stream and may be diverted to the sample stream. When the valve is in the first position and the second position, the lumen and the primary product collection vessel may be in fluid isolation of the sample stream.

In some examples, the fluid processing assembly may further comprise a tube. The tube may form the lumen.

In some examples, the energizing device may comprise an irradiating device irradiating an irradiation zone. The energizable portion may be within the irradiation zone. The irradiating device may comprise a microwave irradiating device. The energizable portion may be positioned exterior to the primary product collection assembly. The portion of the primary product collection assembly may be non-transparent to microwaves.

According to another aspect, a method for processing fluids comprises: a) pressurizing a lumen and at least a portion of a primary product collection assembly; b) flowing at least one inlet stream into the lumen; c) supplying energy to at least a portion of the inlet stream in an energizable portion of the lumen; d) dispensing a product stream from the lumen and directing the product stream into the portion of the primary product collection assembly; and e) periodically diverting a sample of the primary product stream away from the primary product collection assembly, while maintaining the pressure in the lumen and the portion of the primary product collection assembly.

In some examples, step d) may comprise flowing the product stream through a valve.

In some examples, step e) may comprise periodically (i) moving the valve a first time to isolate a plug from the product stream; and (ii) after step (i), moving the valve a second time to divert the plug to a sample stream. During steps (i) and (ii), the lumen and the portion of the primary product collection vessel may be in fluid isolation of the sample stream.

In some examples, the method may comprise directing the plug from the sample stream into a sample collection vessel.

In some examples, step c) may comprise irradiating the energizable portion of the lumen.

According to another aspect, a fluid processing assembly comprises a pressurized primary product stream flowing towards a pressurized portion of a primary product collection assembly, and a sample stream having an inlet end portion and an outlet end portion. The inlet end portion is connectable in fluid communication with the primary product stream upstream of the primary product collection assembly for receiving a sample of the product. An automatic actuator is coupled to the outlet end portion. The automatic actuator is operable to move the outlet end towards and away from a dispensing position. The fluid processing assembly further comprises a sample collection vessel. The outlet end portion is in fluid communication with the sample collection vessel when in the dispensing position. An analysis apparatus is operable to receive at least a portion of the sample of the product, and analyze the portion.

In some examples, the fluid processing assembly may further comprise a pressurized lumen upstream of the product collection vessel for receiving at least one inlet stream and dispensing the pressurized product stream;

In some examples, the fluid processing assembly may further comprise an energizing device for supplying energy to an energizable portion of the lumen.

In some examples, the fluid processing assembly may further comprise a valve positioned in the primary product stream. The valve may be movable to divert the sample into the sample stream while maintaining the pressure in the portion of the primary product collection assembly and the primary product stream. The valve may be a multi-port multi-position valve.

In some examples, the outlet end portion may comprise a needle, and the needle may be inserted into the sample collection vessel when the outlet end portion is in the dispensing position.

In some examples, the fluid processing assembly may further comprise a gas injection line connectable in fluid communication with the sample collection vessel for injecting gas into the sample collection vessel, and a gas withdrawal line connectable in fluid communication with the sample collection vessel for removing gas from the sample collection vessel. The automatic actuator may be coupled to the gas injection line and gas withdrawal line for connecting the gas injection line and gas withdrawal line in fluid communication with the sample collection vessel.

According to another aspect, a method for collecting and analyzing a sample comprises: a) flowing a pressurized primary product stream towards a pressurized portion of a primary product collection assembly; b) diverting a sample of the primary product stream into a sample stream; c) automatically dispensing the sample into a sample collection vessel; and d) withdrawing at least a portion of the sample from the sample collection vessel and analyzing the sample.

In some examples, step c) may comprise engaging an automatic actuator to place an outlet end of the sample stream in fluid communication with the sample collection vessel. The outlet end of the sample stream may comprise a needle, and step c) may further comprise inserting the needle through a stopper of the sample collection vessel.

In some examples, the method may further comprise processing the sample between steps c) and d).

In some examples, the method may further comprise at least one of (i) automatically injecting gas into the sample collection vessel, and (ii) automatically withdrawing gas from the sample collection vessel.

In some examples, step b) may comprise actuating a multi-port multi-position valve to divert the sample of the product into the sample stream. Step b) may further comprise maintaining the pressure in the primary product stream.

In some examples, prior to step a), the method may further comprise: flowing at least one inlet stream into a pressurized lumen; supplying energy to at least a portion of the inlet stream in an energizable portion of the lumen; and dispensing the primary product stream from the lumen.

According to another aspect, a fluid processing assembly comprises a lumen for receiving at least one inlet stream and dispensing a primary product stream, and an energizing device for supplying energy to an energizable portion of the lumen. A primary product collection assembly has at least a portion in fluid communication with the lumen for receiving the primary product stream. The primary product collection assembly continuously dispenses a bulk product. A pressurized gas source pressurizes the lumen and the portion of the primary product collection assembly. At least one bulk product collection assembly is provided for receiving the bulk product. The at least one bulk product collection assembly is at atmospheric pressure. The lumen remains pressurized while the bulk product is dispensed to the bulk product collection assembly.

In some examples, the primary product collection assembly may comprise a first primary product collection vessel and a second primary product collection vessel, and a valve downstream of the lumen and upstream of the first primary product collection vessel and the second primary product collection vessel. The valve may be movable between a first position and a second position. The valve may direct the primary product stream to the first primary product collection vessel when in the first position, and to the second primary product collection vessel when in the second position.

In some examples, the pressurized gas source may be selectively connectable to the first primary product collection vessel and the second primary product collection vessel. The pressurized gas source may pressurize the first primary product collection vessel and the lumen when the valve is in the first position and the pressurized gas source is connected to the first primary product collection vessel. The pressurized gas source may pressurize the second primary product collection vessel and the lumen when the valve is in the second position and the pressurized gas source is connected to the second primary product collection vessel.

In some examples, the bulk product collection assembly may comprise a first bulk product collection vessel for receiving the bulk product from the first primary product collection vessel, and a second bulk product collection vessel for receiving the bulk product from the second primary product collection vessel.

In some examples, the primary product collection assembly may comprise a valve downstream of the lumen for receiving the primary product stream. The valve may comprise a first loop and a second loop. The valve may be connected to the bulk product collection assembly, the pressurized gas source, and a pump.

In some examples, the first loop and second loop may be variable in size.

In some examples, the valve may be movable between a first position and a second position. When the valve is in the first position, the first loop may be in fluid communication with the lumen and the pressurized gas source, and the second loop may be in fluid communication with the pump and the bulk product collection assembly. When the valve is in the second position, the first loop may be in communication with the pump and the bulk product collection assembly, and the second loop may be in communication with the lumen and the pressurized gas source.

In some examples, the fluid processing assembly may also include a recycle line fluidly connecting the pressurized gas source and the pump to permit the flow of fluid from the pressurized gas source to the pump, and it may include a unidirectional flow regulating apparatus to prevent back flow of fluid through the recycle line from the pump to the pressurized gas source.

In some examples, the fluid processing assembly may include a fluid removal line fluidly connected to the pressurized gas source to permit removal of fluid from the pressurized gas source, and it may include a pressure controlling device positioned in the fluid removal line to permit removal of the fluid from the pressurized gas source while maintaining the pressure in the portion of the primary product collection vessel and the lumen.

According to another aspect, a method for processing fluids comprises: a) supplying a pressurized gas to a primary product collection assembly to pressurize at least a portion of the primary product collection assembly and a lumen upstream of the primary product collection assembly; b) flowing at least one inlet stream into the lumen; c) supplying energy to an energizable portion of the lumen, d) continuously dispensing a primary product stream from the lumen into the primary product collection assembly; and e) continuously dispensing a bulk product from the primary product collection assembly while maintaining the pressure in the lumen.

In some examples, step a) may comprise alternately: supplying the pressurized gas to a first primary product collection vessel of the primary product collection assembly; and supplying the pressurized gas to a second primary product collection vessel of the primary product collection assembly In some examples, step d) may comprise alternately: dispensing the primary product stream into the first primary product collection vessel while the pressurized gas is supplied to the first primary product collection vessel, and maintaining the primary product stream in fluid isolation of the second primary product collection vessel; and dispensing the primary product stream into the second primary product collection vessel while the pressurized gas is supplied to the second primary product collection vessel, and maintaining the primary product stream in fluid isolation of the first primary product collection vessel.

In some examples, step e) may comprise alternately: dispensing a first bulk product stream from the first primary product collection vessel while the primary product stream is dispensed into the second primary product collection vessel and pressurized gas is supplied to the second primary product collection vessel; and dispensing a second bulk product stream from the second primary product collection vessel while the primary product stream is dispensed into the first primary product collection vessel and pressurized gas is supplied to the first primary product collection vessel.

In some examples step a) may comprise alternately: connecting a first loop of a valve of the primary product collection assembly in fluid communication with the lumen and in fluid communication with the pressurized gas source; and connecting a second loop of the valve in fluid communication with the lumen and in fluid communication with the pressurized gas source.

In some examples, step d) may comprise alternately: dispensing the primary product stream from the lumen into the first loop of the valve when the first loop is in fluid communication with the lumen; and dispensing the primary product stream from the lumen into the second loop of the valve when the second loop is in fluid communication with the lumen.

In some examples, the valve may be a multi-port multi-position valve. Steps a) and d) may comprise repeatedly actuating the valve to alternately connect the first loop and second loop in fluid communication with the lumen and the pressurized gas source In some examples, step e) may comprise alternately: connecting the first loop to a pump and to a bulk product collection vessel to dispense the contents of the first loop into the bulk product collection vessel; and connecting the second loop to the pump and to the bulk product collection vessel to dispense the contents of the second loop into the bulk product collection vessel.

In some examples, the valve may be a multi-port multi-position valve. Step e) may comprise repeatedly actuating the valve to alternately connect the first loop and second loop in fluid communication with the pump and the bulk product collection vessel.

BRIEF DESCRIPTION OF THE DRAWINGS

The drawings included herewith are for illustrating various examples of articles, methods, and apparatuses of the present specification and are not intended to limit the scope of what is taught in any way. In the drawings.

DETAILED DESCRIPTION

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses described below. It is possible that an apparatus or process described below is not an embodiment of any exclusive right granted by issuance of this patent application. Any invention disclosed in an apparatus or process described below and for which an exclusive right is not granted by issuance of this patent application may be the subject matter of another protective instrument, for example, a continuing patent application, and the applicants, inventors or owners do not intend to abandon, disclaim or dedicate to the public any such invention by its disclosure in this document.

Figure 1:
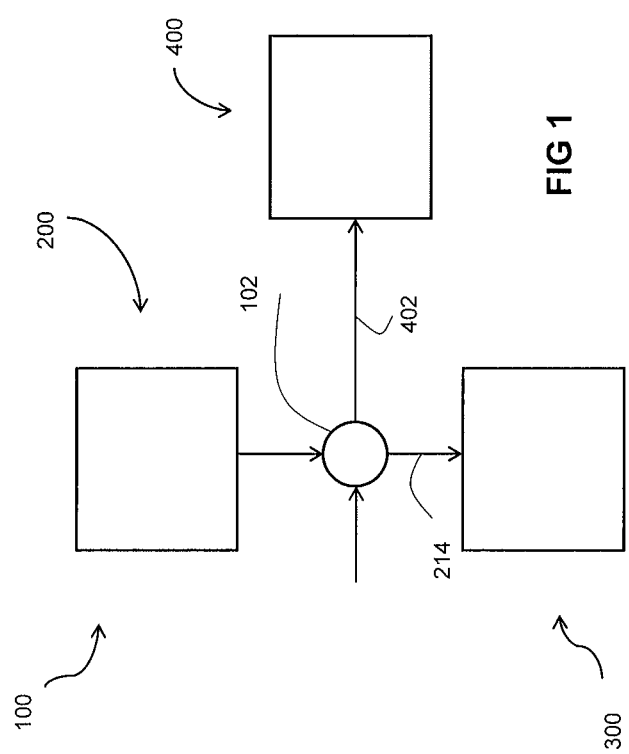
FIG. 1 is a flow diagram of an example fluid processing assembly.

Referring to FIG. 1, an example fluid processing assembly 100 is shown. The fluid processing assembly 100 generally includes a reactor assembly 200, a product collection assembly 300, and a sample collection assembly 400.

Figure 2:
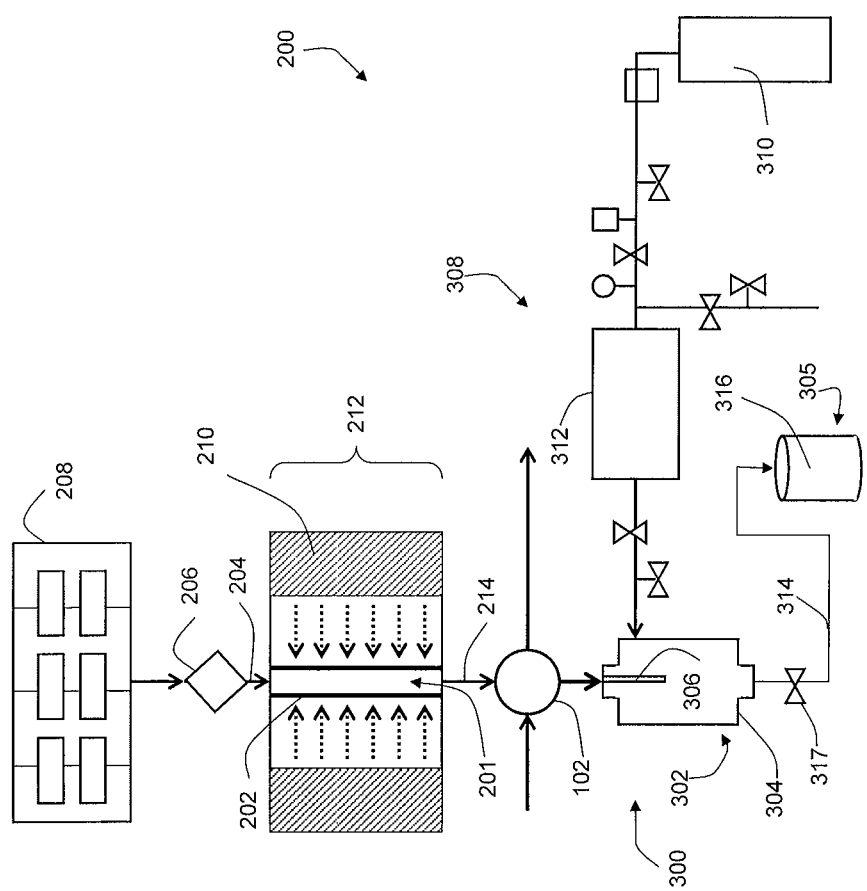
FIG. 2 is a flow diagram of the reactor assembly and product collection assembly of the fluid processing assembly of FIG. 1.

Referring to FIG. 2, the reactor assembly 200 includes a lumen 201, within which a reaction occurs. In the example shown, the lumen 201 is formed by a tube 202. In some examples, the tube may be a capillary, for example a glass capillary. As will be described in further detail below, the lumen 201 may be pressurized by a downstream pressurized gas source (i.e. back pressure may be applied to the lumen). Optionally, the lumen may be of any suitable construction, including, for example, a capillary, a tube/conduit of any suitable cross-section (round, square, etc), and a channel in a chip. Further, the lumen may be formed from any suitable material in whole or in part, including microwave radiation transparent materials (such as glass or alumina) whereby the microwave irradiation directly heat the product material, and/or microwave radiation absorbing materials (such as silicon carbide, graphite, charcoal, etc.) whereby the microwaves heat the lumen material which then heats the reactant/product material contained in the lumen.

Referring still to FIG. 2, in the example shown, the lumen 201 receives an inlet stream 204. The inlet stream 204 flows into the lumen 201 from a mixer 206, which is in communication with a material supply array 208. In alternate examples, the lumen 201 may receive more than one inlet stream, and mixing may occur within the lumen 201.

Referring still to FIG. 2, the reactor assembly 200 further includes an energizing device 210 for supplying energy to an energizable portion 212 of the lumen 201. In some examples, the energizing device may be an irradiating device which irradiates an irradiation zone, and the energizable portion 212 may be within the irradiation zone. For example, as shown in FIG. 2, the energizing device 210 is a microwave irradiating device 210. The microwave irradiating device 210 irradiates the energizable portion 212 of the lumen 201 with microwave irradiation. The microwave irradiation device can heat the contents of the energizable portion 212 of the lumen 201, and may facilitate a reaction. For example, the material supply array 208 and mixer 206 may provide a solution of reactants to the lumen 201. When heated in the energizable portion 212 of the lumen 201 by the microwave irradiating device 210, the reactants may undergo a chemical reaction to yield one or more products. As mentioned above, the lumen 201 may be pressurized in order to facilitate the reaction. For example, the lumen may be pressurized in order to prevent or inhibit a phase change within the lumen, and to maintain the reactants in the liquid phase, which may facilitate the reaction.

In the example shown, the microwave irradiating device 210 supplies energy to essentially the entirety of the lumen 201, and the entirety of the lumen 201 may be considered to be the energizable portion 212. In other examples, only a portion of the lumen 201 may be the energizable portion. For example, the inlet and outlet ends of the lumen 201 may be positioned such that they are outside of the irradiation zone, and are not irradiated by the microwave irradiating device.

As mentioned above, in some examples, a chemical reaction may occur within the lumen 201. In other examples, other types of reactions may occur in the lumen 201. Such reactions may include, for example, pasteurization sterilization, or fluid derivation.

As mentioned above, in some examples, the energizing device may be a microwave irradiating device. In other examples, the energizing device may be an ultrasound device, a photo device such as a light, or a thermal device such as a heat exchanger, oven, resistive heating, inductive heaters, photo irradiation or heating tape.

Referring still to FIG. 2, a primary product stream 214, containing the product(s) of the reaction, is dispensed from the lumen 201 and is directed to the product collection assembly 300. In the example shown, the product collection assembly 300 includes a primary product collection assembly 302, and a downstream bulk product collection assembly 305. The primary product collection assembly 302 is in fluid communication with the lumen 201 for receiving the primary product stream 214. In the example illustrated, at least a portion of the primary product collection assembly is pressurized by a pressurized gas source, which applies back pressure to the lumen 201. The downstream bulk product collection assembly 305 is, in the example illustrated, at atmospheric pressure.

Referring still to FIG. 2, in the example shown, the primary product collection assembly 302 includes a primary product collection vessel 304. The primary product collection vessel 304 is pressurized and is generally sealed to the external atmosphere (i.e. in the example shown, the primary product collection vessel 304 is the portion of the primary product collection assembly 302 that is pressurized). A drip tube 306 is mounted within the primary product collection vessel 304. The drip tube 306 receives the primary product stream 214, and the primary product stream 214 drips from the drip tube 306 into the primary product collection vessel 304.

As mentioned above, in the example shown, the primary product collection vessel 304 is pressurized by a pressurized gas source, which in turn pressurizes (i.e. applies back pressure to) the primary product stream 214 and the lumen 201, and in order to facilitate the reaction in the lumen 201. When using conventional physical backpressure regulators, contact between the product stream and regulator can result in fouling of the regulator, which in some instances may interrupt the operation of the system. This may cause premature halting of a production run. In the example illustrated, backpressure is applied to the system by pressurizing the primary collection vessel 304, via a pressurized gas, with a sufficiently high pressure gradient to prevent backflow of product liquid into the gas system, and the liquid product stream is dripped into the pressurized primary product vessel 304 which eliminates the need for direct physical contact between a back pressure regulator and the product stream.

In the example shown, a pressurized gas source 308 is connected to and supplies pressurized gas to the primary product collection vessel 304 to pressurize the primary product collection vessel 304, the drip tube 306, the primary product stream 214 and the lumen 201. In order to maintain flow from the lumen 201 to the primary product collection vessel 304, the inlet stream 204 may be pressurized at a greater pressure than the back pressure supplied by the pressurized gas source. For example, one or more pumps (not shown) may be used to direct the inlet stream 204 into the lumen 201 at a greater pressure than the back pressure supplied by the pressurized gas source.

The pressurized gas source may be of any suitable configuration. In the example shown, the pressurized gas source 308 includes a gas supply tank 310, a pressure ballast 312, and various check valves, shut-off valves, vents, and regulators. The pressurized gas may be, in some examples, an inert gas such as nitrogen or argon. In other examples, the pressurized gas may be a reactive gas, and may, for example, participate in the reaction it the lumen.

In some examples, the reactor assembly 200 may be operated continuously, and the product collection assembly 300 may be operated semi-continuously. Specifically, in the example shown, the reactor assembly 200 may be operated continuously, and the primary product collection vessel 304 may continuously receive the primary product stream 214 and semi-continuously dispense a bulk product stream 314 to the bulk product collection assembly 305. More specifically, in the example shown, the product collection assembly 300 is configured such that the primary product stream 214 may continuously build up delivered product in the primary product collection vessel 304, until a desired volume is reached. When the desired volume is reached, the supply of pressurized gas may be shut-off, and an outlet valve 317 of the primary product collection vessel 304 may be opened to de-pressurize the system and to dispense the bulk product stream 314 from the primary product collection vessel 304 into a bulk product collection vessel 316 of the bulk product collection assembly 305. The outlet valve 317 may then be closed, and the system may be re-pressurized.

In alternate examples, the reactor assembly and product collection assembly may both be operated continuously. Specifically, as will be described in further detail below, the primary product collection assembly may be configured to continuously dispense the bulk product stream into the bulk product collection vessel without depressurizing the system, so that the system can be run continuously.

Referring still to FIG. 2, in the example shown, the energizable portion 212 of the lumen 201 is positioned exterior to the primary product collection assembly 302, and more specifically, exterior to the primary product collection vessel 304. In other words, the energizable portion 212 of the lumen 201 is not housed within the primary product collection vessel 304. The primary product collection vessel 304 may therefore optionally be non-transparent to microwave irradiation and/or more chemically resistant. For example the primary product collection vessel 304 may be made from a metal, metallic material or other material that is not suitable for use in forming the lumen 201. This may allow the product collection vessel 304 to have different mechanical and/or chemical properties from the lumen 201. For example the product collection vessel 304 may have higher heat resistance, greater strength, greater durability, and/or a greater chemical resistance, etc.

Referring back to FIG. 1, the fluid processing assembly 100 further includes a valve 102 (also referred to as a sample valve) downstream of the lumen 201 and upstream of the primary product collection assembly 302, through which the primary product stream 214 flows. The valve is useable to divert a sample of the primary product stream 214 away from the primary product collection assembly 302 and to the sample collection assembly 400. In the example shown, the valve 102 is configured to divert the sample without de-pressurizing the primary product collection vessel 304 and the lumen 201.

Figure 3:
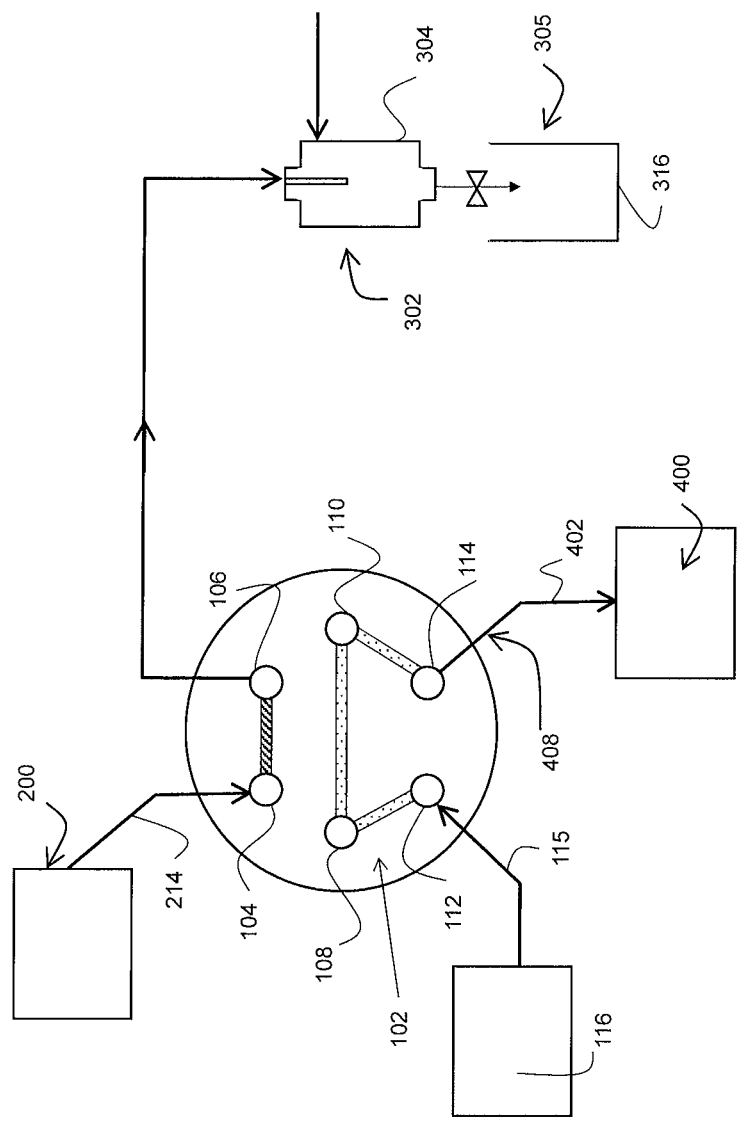
FIG. 3 is a flow diagram of a sample valve of the fluid processing assembly of FIG. 1, showing the sample valve in a first position.
Figure 4:
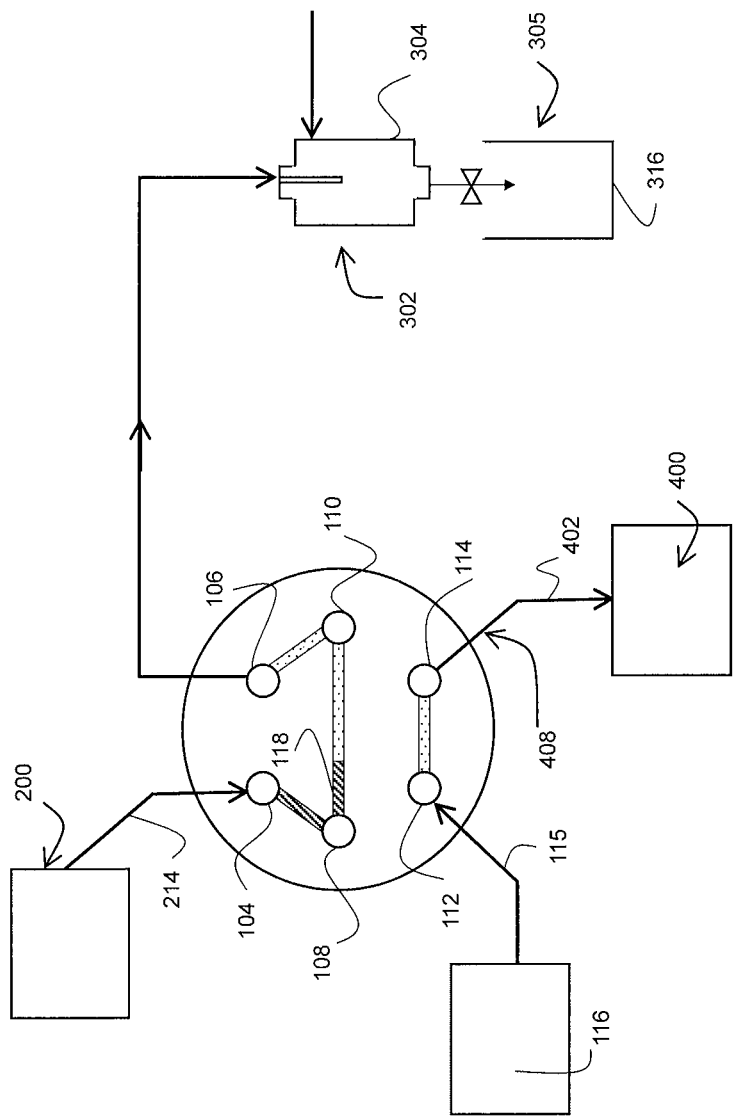
FIG. 4 is a flow diagram of the sample valve of FIG. 3, showing the sample valve in a second position.
Figure 5:
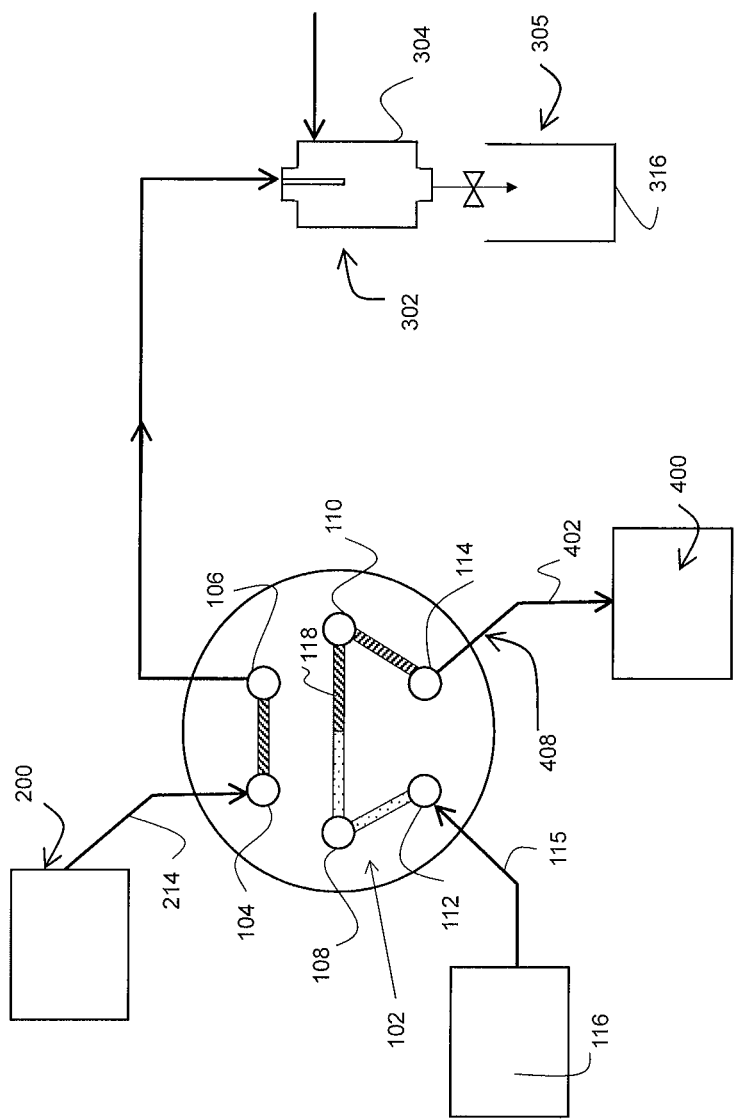
FIG. 5 is a flow diagram of the sample valve of FIG. 4, showing the sample valve moved back to the first position from the second position.

Referring to FIGS. 3 to 5, in the example shown, the valve 102 is a multi-port multi-position valve. The valve 102 is movable to direct the primary product stream 214 from the lumen 201 (shown in FIG. 2) to the primary product collection assembly 302, isolate a plug 118 from the primary product stream 214, and divert the plug 118 to a sample stream 402 of the sample collection assembly 400, while generally maintaining the pressure in the lumen 201 and the primary product collection vessel 304. As used herein, the phrase "maintaining the pressure" indicates that that while insignificant pressure fluctuations that do not materially affect the process may occur, substantial changes in pressure, such as depressurization to atmospheric pressure, do not occur. In the example shown, the valve 102 is a 6-port 2-position valve, and includes ports 104, 106, 108, 110, 112, and 114. The lumen 201 is in fluid communication with port 104, and the primary product collection assembly 302 is in fluid communication with port 106. A liquid solvent stream 115 from a solvent pump 116 is in fluid communication with port 112, and the sample stream 402 of the sample collection assembly 400 is in communication with port 114. The liquid solvent material, like the liquid product material is generally understood to be incompressible, which can help facilitate pressurization of the system.

In the example shown, the valve 102 is movable between a first position, shown in FIGS. 3 and 5, and a second position, shown in FIG. 4. Referring to FIG. 3, when the valve 102 is in the first position, port 104 and port 106 are in fluid communication, and the primary product stream 214 is directed from the lumen 201 to the primary product collection assembly 302. Further, when the valve 102 is in the first position, ports 108, 110, 112, and 114 are in fluid communication, and solvent is directed from the solvent pump 116 to the sample stream 402. Referring to FIG. 4, when the valve 102 is moved to the second position, ports 104, 108, 110, and 106 are in fluid communication, and a loop defined between ports 108 and 110 is positioned in fluid communication with the reactor assembly 200 and is populated with liquid plug 118 from the primary product stream 214. While the system is in operation, the loop between ports 108 and 110 can become partially and/or completely filled with the reactant/product stream. Further, when the valve 102 is in the second position, ports 112 and 114 are in fluid communication, and solvent continues to be directed from the solvent pump 116 to the sample stream 402. Referring to FIG. 5, when the valve 102 is moved back to the first position, the primary product stream 214 is again directed from the lumen 201 to the primary product collection assembly 302, and the plug 118 is isolated from the primary product stream 214 and can be pushed with solvent from the solvent pump 116 towards to the sample stream 402. Optimally, in between collections, clean solvent can be pushed through the loop between ports 108 and 110 which may help clean the loop.

As can be seen in FIGS. 3 to 5, whether the valve 102 is in the first position or the second position, the lumen 201 is in fluid communication with the primary product collection vessel 304, and in fluid isolation of the sample stream 402 and the exterior atmosphere.

In use, when the reactor assembly 200 is in operation, the valve 102 may be periodically moved from the first position to the second position (i.e. moved a first time), and from the second position back to the first position (i.e. moved a second time), in order to divert a sample of the primary product stream 214 away from the primary product collection assembly 302 and towards the sample collection assembly 400, while maintaining the pressure in the lumen 201 and the primary product collection vessel 304.

Figure 6:
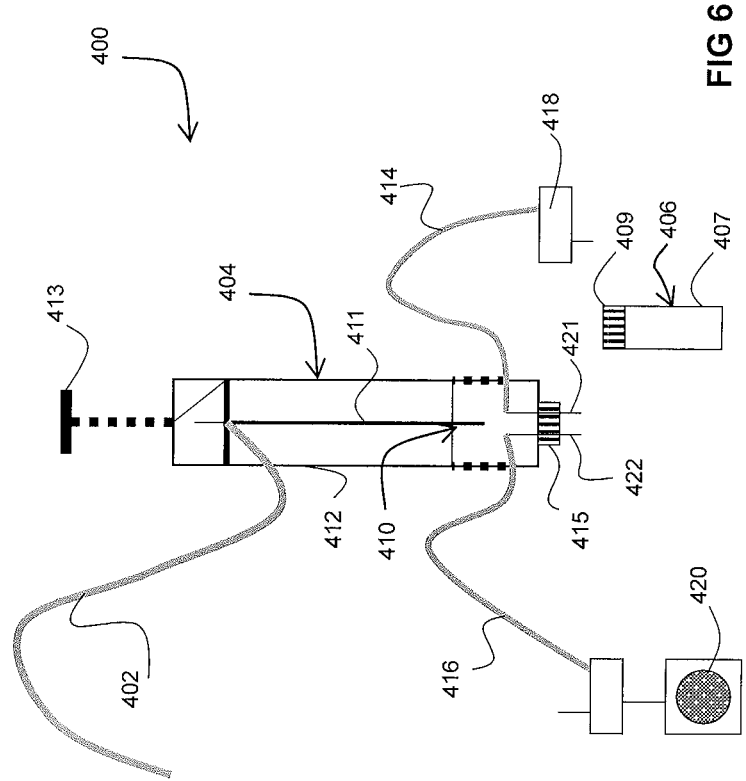
FIG. 6 is a schematic diagram of the sample collection assembly of FIG. 1, showing an actuator in a home position.

Referring now to FIG. 6, an example sample collection assembly 400 is shown in further detail. The sample collection assembly 400 generally includes the sample stream 402, an automatic actuator 404, and a sample collection vessel 406.

Referring still to FIG. 6, the sample stream 402 includes an inlet end portion 408 (shown in FIGS. 3 to 5), and an outlet end portion 410. The inlet end portion 408 is connectable in fluid communication with the primary product stream 214 upstream of the primary product collection assembly 302 for receiving a sample of the product. In the example shown, the inlet end portion 408 is connected to port 114 of the valve 102, so that when the valve 102 is moved from the first position, to the second position, and back to the first position, the inlet end portion 408 receives a sample of the primary product stream 214. The outlet end portion 410 of the sample stream 402 includes a fluid delivery conduit, which in the example illustrated is provided as a needle 411, which may be inserted into the sample collection vessel 406, as will be described in further detail below.

Referring still to FIG. 6, in the example shown, the sample collection vessel 406 includes a glass vial 407 having a piercable stopper 409. In other examples, the sample collection vessel 406 may be another suitable vessel, such as a test tube.

Figure 9:
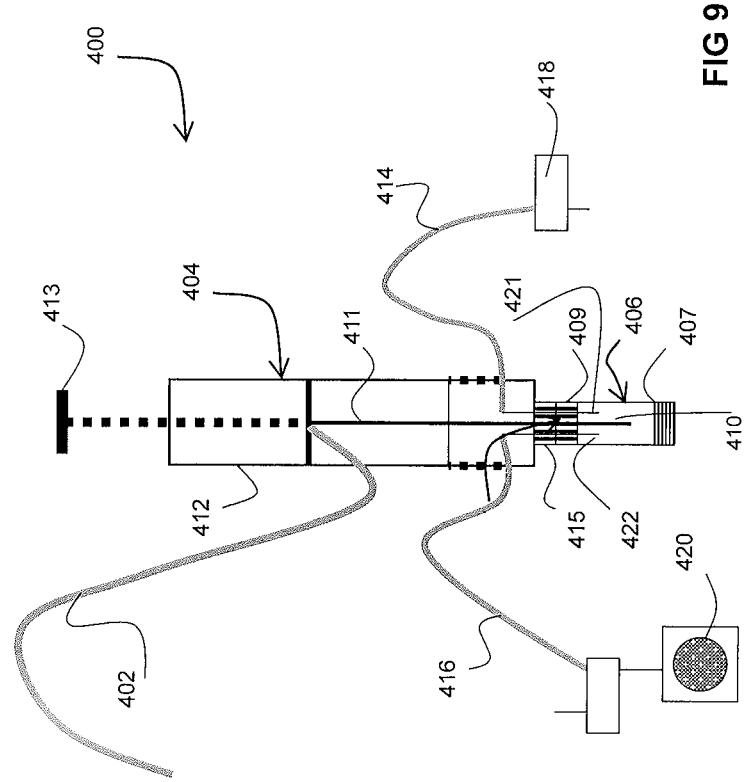
FIG. 9 is a schematic diagram of the sample collection assembly of FIG. 8, showing the outlet end of a sample stream in a dispensing position.

Referring now to FIGS. 6 and 9, the automatic actuator 404 is coupled to the outlet end portion 410, and is operable to move the outlet end portion 410 towards and away from a dispensing position (the dispensing position is shown in FIG. 9). Referring to FIG. 9, when the outlet end portion 410 is in the dispensing position, the needle 411 is inserted through the stopper 409 of the sample collection vessel 406, so that the outlet end portion 410 is in fluid communication with the sample collection vessel 406.

In the example shown, the automatic actuator includes a movable frame 412 in which the needle is mounted, a robot (not shown) for moving the frame 412, a motor 413 for moving the needle 411 within the frame, and a vessel grip 415 for gripping the sample collection vessel 406

In the example shown, the sample collection assembly 400 further includes a gas injection line 414 connectable in fluid communication with the sample collection vessel 406 for injecting gas into the sample collection vessel 406, and a gas withdrawal line 416 connectable in fluid communication with the sample collection vessel 406 for removing gas from the sample collection vessel 406. The gas injection line 414 may be connected to a gas source 418, such as an inert gas. The gas withdrawal line 416 may be connected to a vacuum pump 420. Both the gas injection line 414 and the gas withdrawal line 416 include a needle 421, 422, respectively, which may be inserted through the stopper of the sample collection vessel 406.

Figure 7:
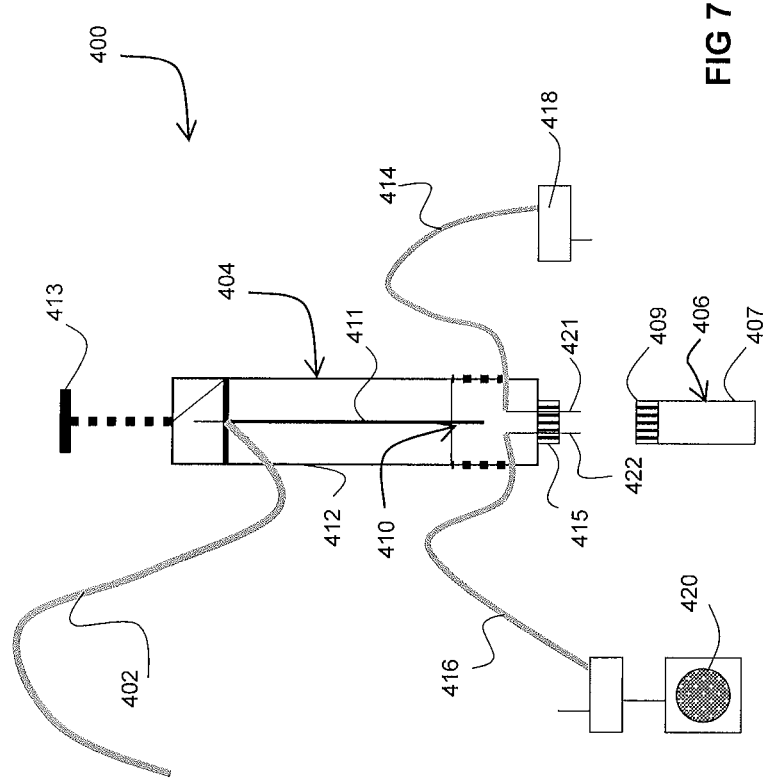
FIG. 7 is a schematic diagram of the sample collection assembly of FIG. 6, showing the actuator moved towards a sample collection vessel.
Figure 8:
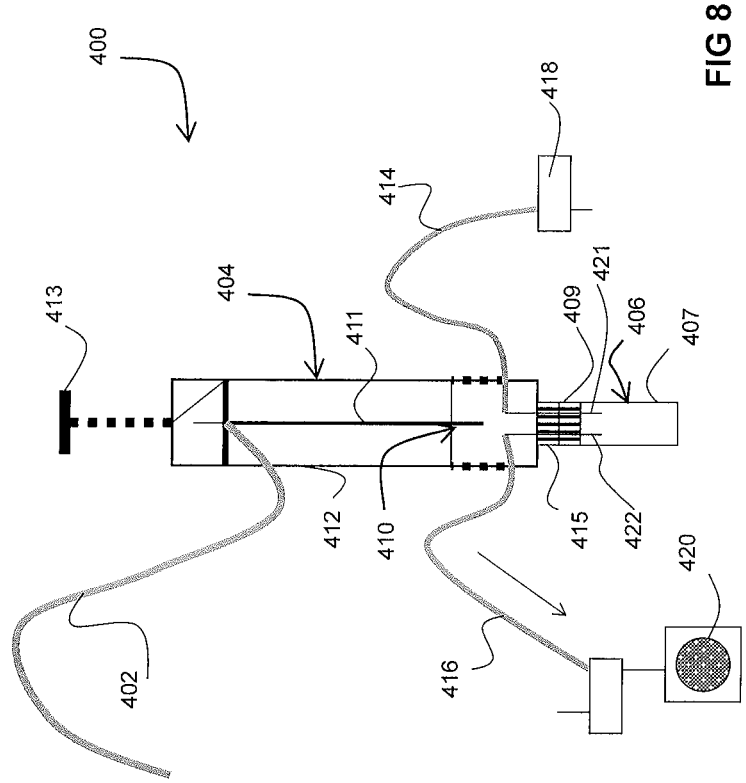
FIG. 8 is a schematic diagram of the sample collection assembly of FIG. 7, showing the actuator gripping a sample collection vessel.

Referring now to FIGS. 6 to 9, an example series of steps for operating the sample collection assembly 400 will be described. The steps may be under automatic control, or may be carried out manually. In examples where the steps are under automatic control, the timing of the various steps may be based on the status of the valve 102. For example, the steps may be initiated when the valve 102 is actuated to divert a sample to the sample stream 402. Referring to FIGS. 6 to 8, when the plug 118 of the sample is approaching the outlet end portion 410 of the sample stream 402, the robot may be engaged to move the frame 412 from a home position (shown in FIG. 6), towards the sample collection vessel 406 (as shown in FIG. 7). The robot may then move the frame 412 downwardly so that the needles 421, 422 are inserted through the stopper 409 of the sample collection vessel 406, and so that the vessel grip 415 grips the sample collection vessel 406 (as shown in FIG. 8). The vacuum pump 420 may then be activated to purge the sample collection vessel 406 of the gas contained therein, and to fill the sample collection vessel 406 with the gas from the gas source 418 (e.g. an inert gas). The motor 413 may then be actuated to move the needle 411 to the dispensing position, as shown in FIG. 9, so that the sample is dispensed into the sample collection vessel 406.

In some examples, the sample collection assembly 400 may include a sample analysis apparatus (not shown), such as a gas or liquid chromatograph, optionally fitted with suitable technologies such as EI (electron ionization), CI (chemical ionization), ESI (electrospray ionization), APCI (atmospheric pressure chemical ionization), TCD (thermal conductivity detector), FID (flame ion detector), or CCD (catalytic combustion detector). Further examples of analysis apparatuses include NMR, IR, UV-VIS, or PDA (photo diode array) in tandem or in parallel with chromatography. The sample analysis apparatus may be operable to receive at least a portion of the sample of the product, and analyze the sample. For example, the sample collection vessel 406 may be transferred to sample analysis apparatus (for example by the robot), so that the sample analysis apparatus may withdraw a portion of the sample therefrom and analyze the portion. In a further example, a portion of the sample may be transferred from the sample collection vessel 406 to another vessel, which may be received by the sample analysis apparatus. In a further example, the sample collection assembly 400 may be configured to carry out various processing steps on the sample prior to forwarding a portion of the sample to the sample analysis apparatus. For example, various components, such as a solvent and/or a reactant, may be added to or removed from the sample (for example to concentrate the sample).

Data derived from the analyses of the sample analysis apparatus can be provided to a platform of a system control manager platform (not shown) to rationally alter parameters of the fluid processing assembly (e.g., process temperature, flow-rate, stoichiometry, pressure, extracted sample volume, dilution volume, concentration, choice of dilutant, chemical contributors (e.g., reagents, catalysis, solvent, promoter) and any other factors that may influence the process). This may be done, for example, to optimize efficiency and/or minimize safety-related risks. The system control manager may be capable of controlling the fluid processing assembly with built-in artificial intelligence, using basic system algorithms as well as user-defined parameter boundaries. The system control manager platform may also be amenable to manual intervention, either on-site or from a remote location.

Various valves or other components may be positioned in the sample stream 402 between the inlet end portion 408 and the outlet end portion 410. For example a valve may be positioned in the sample stream 402 for diverting the contents thereof to waste.

In alternate examples, the automatic actuator may be without a vessel grip. In some such examples, the frame may be positioned above the vessel, without gripping the vessel, and the various needles may pierce the stopper from this position. In other examples, a vessel guide may be provided instead of a vessel grip. The vessel guide may aid in positioning aligning the frame above the vessel without gripping the vessel.

Figure 10:
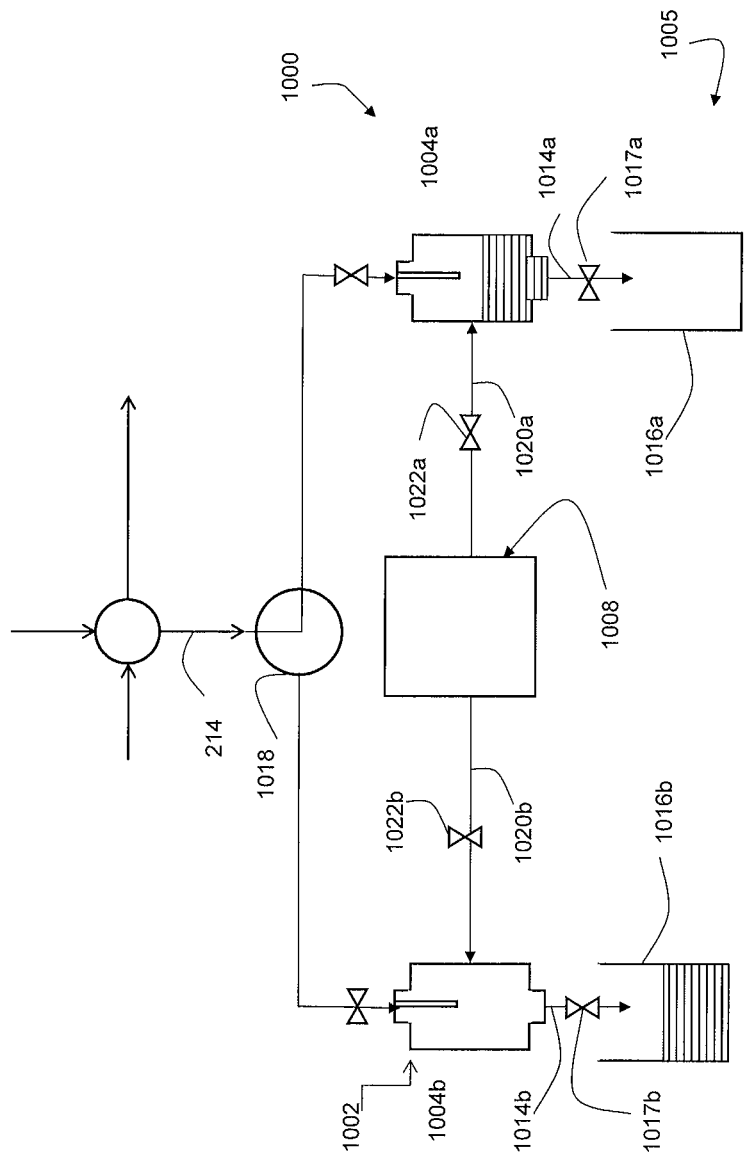
FIG. 10 is a flow diagram of an alternate example of a product collection assembly, showing a shutoff valve in a first position.
Figure 11:
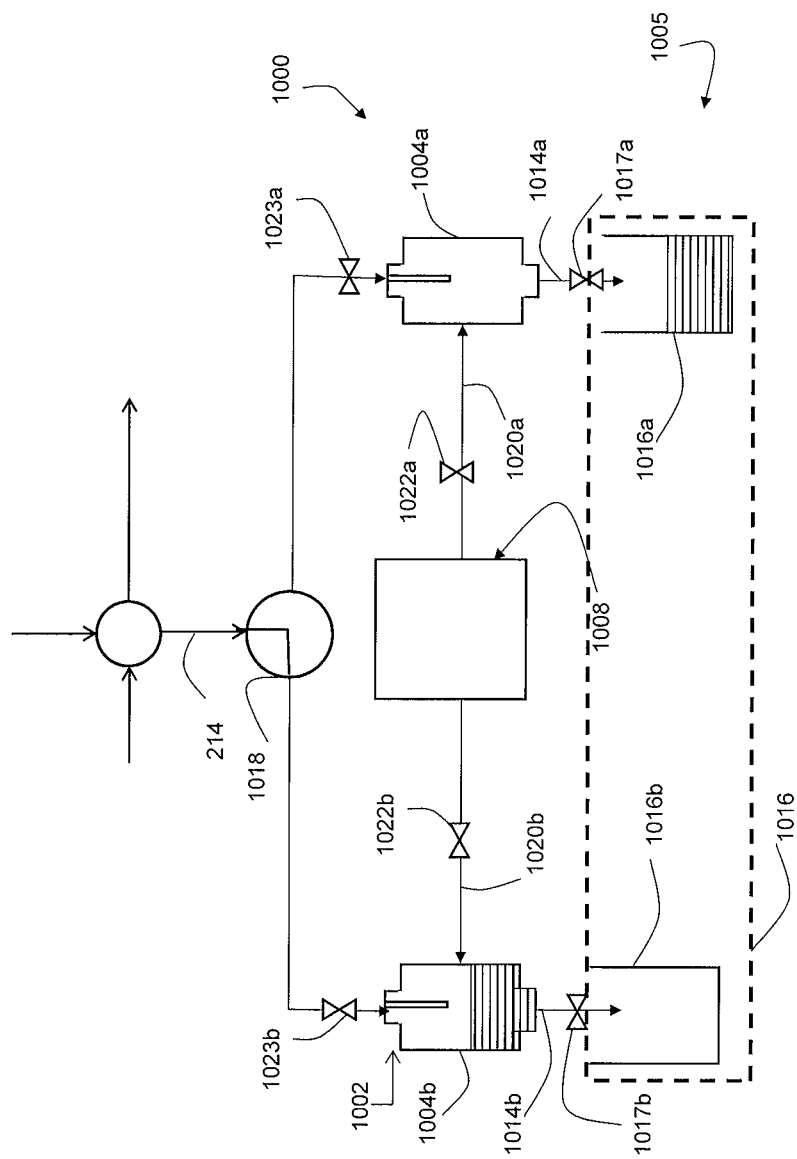
FIG. 11 is a flow diagram of the product collection assembly of FIG. 10, showing the shutoff valve in a second position.

Referring now to FIGS. 10 and 11, an alternate example product collection assembly 1000 is shown, in which like reference numerals, incremented by 700, are used to refer to like features to the product collection assembly 300. The product collection assembly 1000 includes a primary product collection assembly 1002 configured to continuously receive the pressurized primary product stream 214 from the reactor assembly (not shown), and to continuously dispense a bulk product at atmospheric pressure to the bulk product collection assembly 1005, while maintaining the pressure in the lumen 201.

Referring to FIG. 10, the primary product collection assembly 1002 includes a first primary product collection vessel 1004a, and a second primary product collection vessel 1004b. A stream selector valve 1018 is downstream of the lumen 201 and upstream of the first 1004a and second 1004b primary product collection vessels. The stream selector valve 1018 is movable between a first position, shown in FIG. 10, where the primary product stream 214 is directed to the first primary product collection vessel 1004a, and a second position, shown in FIG. 11, where the primary product stream 214 is directed to the second primary product collection vessel 1004b.

Referring still to FIG. 10, a pressurized gas source 1008 is connected to the first primary product collection vessel 1004a via a first pressure line 1020a and a first pressure valve 1022a, and to the second primary product collection vessel 1004b via a second pressure line 1020b and a second pressure valve 1022b. The pressurized gas source 1008 is operable to selectively supply pressurized gas to the first primary product collection vessel 1004a, and/or the second primary product collection vessel 1004b, to pressurize the first primary product collection vessel 1004a, and/or the second primary product collection vessel 1004b, as well as the lumen 201 and the primary product stream 214. Other suitable valving and hardware may be provided in the lines between the product collection vessel 1004a (or 1004b). For example, control valves 1023a and 1023b may be provided between primary collection vessels 1004a and 1004b and the valve 1018. Providing control valves 1023a and 1023b may allow the primary collection vessels 1004a and 1004b to be isolated from the system, which may allow the primary collection vessels 1004a and 1004b to be emptied into the bulk collection vessels 1016a and 1016b without significantly depressurizing the system upstream from the control valves 1023a and 1023b, including portions of the lines provided between the control valves 1023a and 1023b and the valve 1018. This may help prevent pressure surges in the system when the control valves 1023a and 1023b are opened and closed.

Referring still to FIG. 10, the bulk product collection assembly 1005 includes a first bulk product collection vessel 1016a and a second bulk product collection vessel 1016b, both of which are at atmospheric pressure. The first bulk product collection vessel 1016a receives bulk product from the first primary product collection vessel 1004a via a first bulk product stream 1014a, and the second bulk product collection vessel 1016b receives a bulk product from the second primary product collection vessel 1004b via a second bulk product stream 1014b. A first outlet valve 1017a is provided between the first primary product collection vessel 1004a and the first bulk product collection vessel 1016a, and a second outlet valve 1017b is provided between the second primary product collection vessel 1004b and the second bulk product collection vessel 1016b. The first 1017a and second 1017b outlet valves may be selectively opened or closed to control the flow of the bulk product between the first primary product collection vessel 1004a and the first bulk product collection vessel 1016a, and the second primary product collection vessel 1004b and the second bulk product vessel 1016b, respectively. Alternatively, instead of providing two separate vessels 1016a and 1016b, a single bulk product collection vessel 1016 (shown using dashed lines in FIG. 11) may be provided to collection the product from both primary collection vessels. This may be advantageous during production when the product is to be produced and collected as defined batches.

Referring still to FIG. 10, in operation, the stream selector valve 1018 may be positioned in the first position, so that primary product stream 214 is directed to the first primary product collection vessel 1004*a*, and is in fluid isolation of the second primary product collection vessel 1004*b*. Further, the first pressure valve 1022*a* may be positioned so that pressurized gas is supplied to the first primary product collection vessel 1004*a*, and the first outlet valve 1017*a* may be closed, so that the first primary product collection vessel 1004*a*, the lumen 201, and the primary product stream 214 are pressurized. The reactor assembly 200 may be continuously operated, and the primary product stream 214 may flow into the primary product collection vessel 1004*a*.

Referring now to FIG. 11, when a desired volume of product is reached within the first primary product collection vessel 1104*a*, the second pressure valve 1022*b* may be positioned so that pressurized gas is supplied to the second primary product collection vessel 1004*b*, and the second outlet valve 1017*b* may be closed, so that the second primary product collection vessel 1004*b* is pressurized. The stream selector valve 1018 may then be moved to the second position, so that the primary product stream 214 is directed to the second primary product collection vessel 1004*b*, and the pressure in the lumen 201 is maintained. The reactor assembly 200 may continue to be operated, and the primary product stream 214 will flow into and be contained within the second primary product collection vessel 1004*b*.

Referring still to FIG. 11, when the stream selector valve 1018 is in the second position and the primary product stream 214 is in fluid isolation of the first primary product collection vessel 1004*a*, the first pressure valve 1022*a* may be positioned so that the supply of pressurized gas to the first primary product collection vessel 1004*a* is stopped. The first outlet valve 1017*a* may then be opened, so that the product in the first primary product collection vessel 1004*a* flows into the first bulk product stream 1014*a* and is collected in the first bulk product collection vessel 1016*a*.

When a desired volume of product is reached within the second primary product collection vessel 1004*b*, the various valves may be switched back to the positions shown in FIG. 10, so that the lumen 201 remains pressurized and directs the primary product stream 214 to the first primary product collection vessel 1004*a*, and the product in the second primary product collection vessel 1004*b* flows through the second bulk product stream 1014*b* and is collected in the second bulk product collection vessel 1016*b*.

By operating the product collection assembly as described above with respect to FIGS. 10 and 11, the primary product collection assembly 1002 may continuously receive the pressurized primary product stream 214 from the reactor assembly 200, and continuously dispense a bulk product at atmospheric pressure to the bulk product collection assembly 1005, while the pressure in the lumen 201 is maintained.

Figure 12:
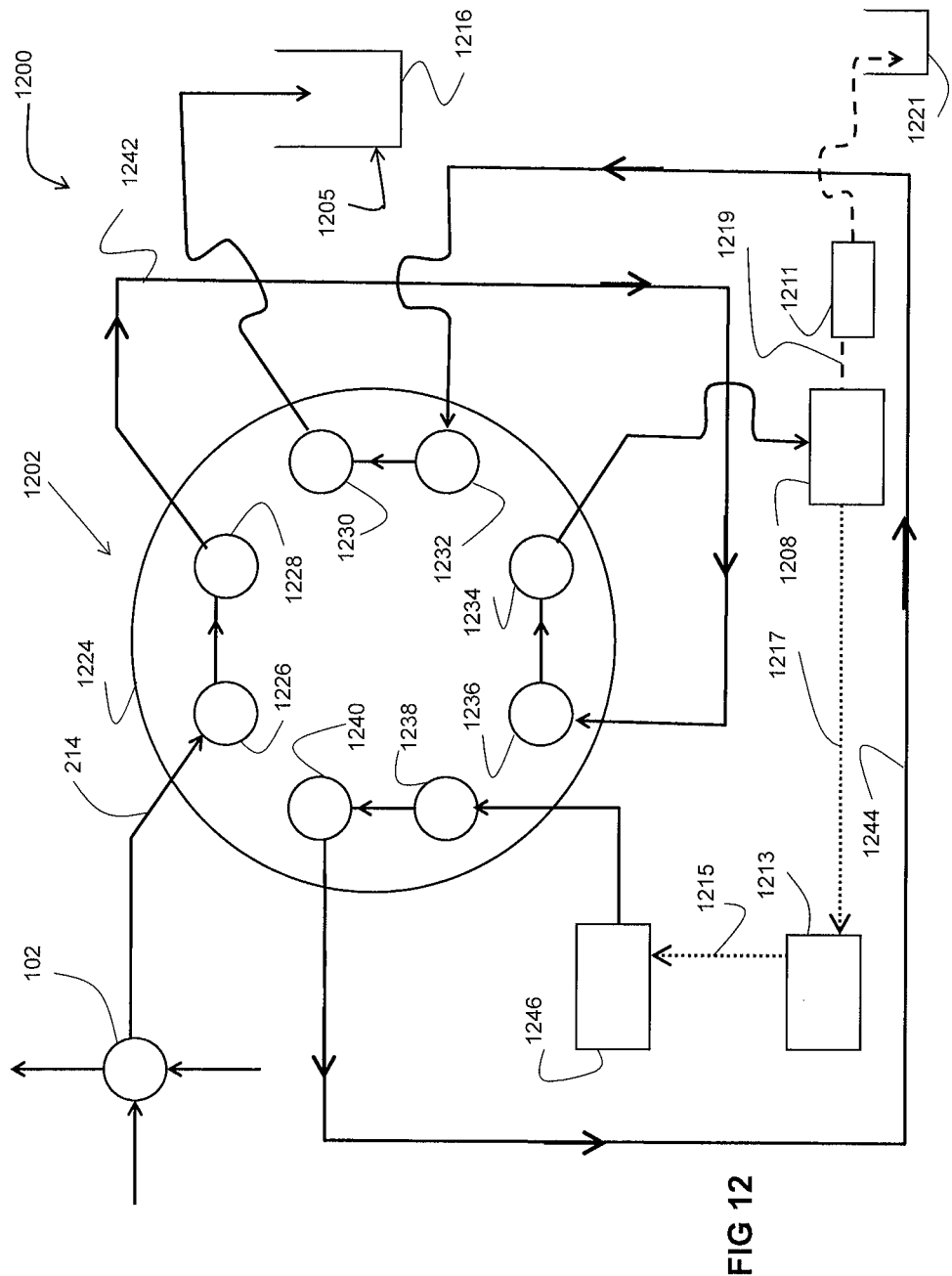
FIG. 12 is a flow diagram of another alternate example of a product collection assembly, showing a primary product collection valve in a first position.
Figure 13:
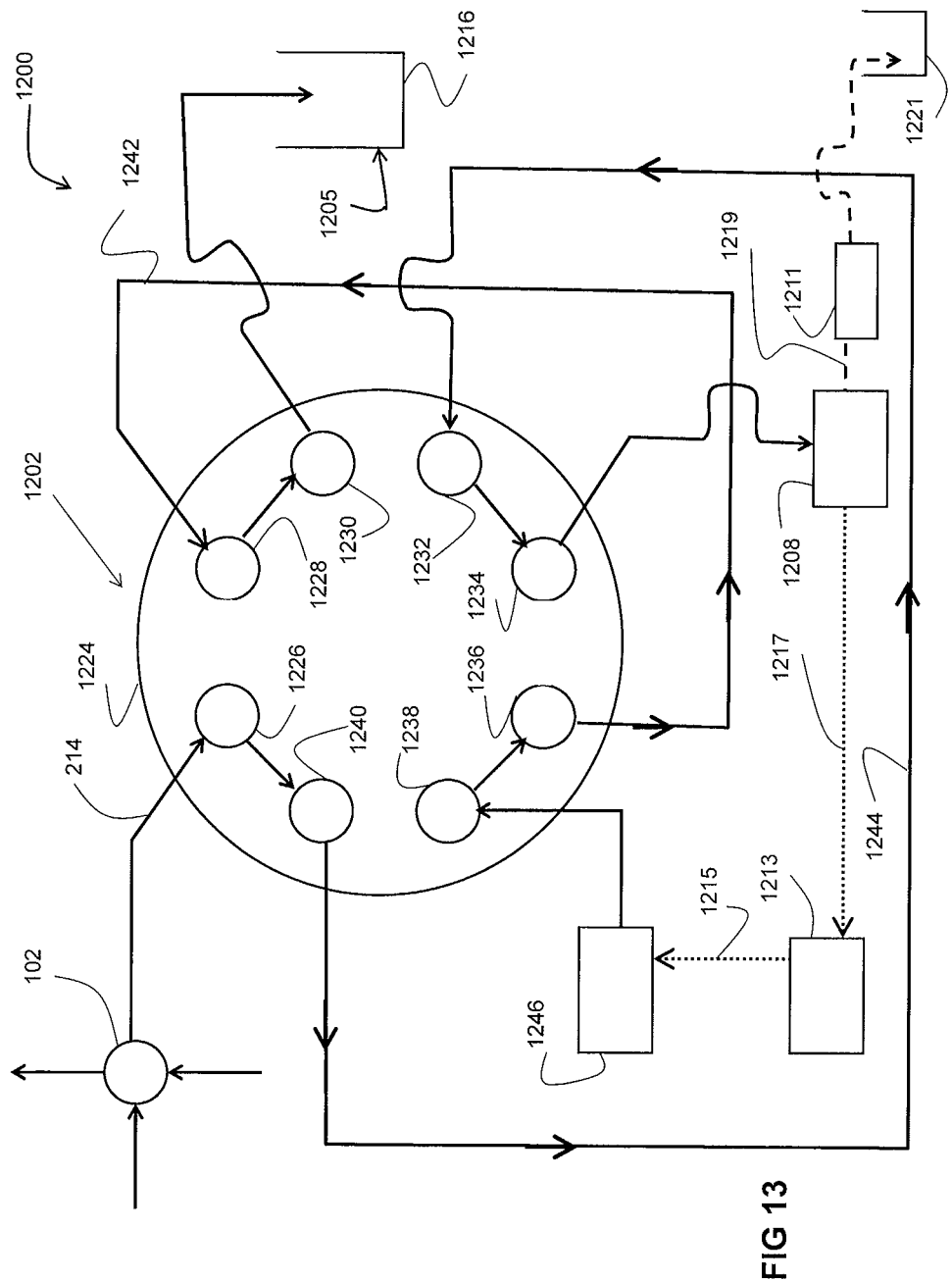
FIG. 13 is a flow diagram of the product collection assembly of FIG. 12, showing the primary product collection valve in a second position.

Referring now to FIGS. 12 and 13, an alternate example product collection assembly 1200 is shown, in which like reference numerals, incremented by 900, are used to refer to like features to the product collection assembly 300. The primary product collection assembly 1202 includes a valve 1224 downstream of the lumen 201 and the sample valve 102 for receiving the primary product stream 214. The valve 1224 may also be referred to as primary product collection valve 1224. Similarly to the example of FIGS. 10 and 11, the primary product collection assembly 1202 is configured to continuously receive the pressurized product stream 214 from the reactor assembly 200, and to continuously dispense a bulk product at atmospheric pressure to the bulk product collection assembly 1205, while maintaining the pressure in the lumen 201.

Referring to FIG. 12, the valve 1224 may be a multi-port multi-position valve. In the example shown, the valve is an eight-port two-position valve, having ports 1226, 1228, 1230, 1232, 1234, 1236, 1238, and 1240. The valve 1224 includes a first loop 1242, between ports 1228 and 1236, and a second loop 1244, between ports 1232 and 1240. Further, port 1226 is connected in fluid communication with the lumen 201 and the primary product stream 214, port 1230 is connected in fluid communication with a bulk product collection vessel 1216 at atmospheric pressure, port 1234 is connected in fluid communication with a pressurized gas source 1208, and port 1238 is connected to a pump 1246.

The valve 1224 is movable between a first position, shown in FIG. 12, and a second position, shown in FIG. 13. Referring to FIG. 12, when in the first position, port 1226 is connected to port 1228, port 1230 is connected to port 1232, port 1234 is connected to port 1236, and port 1238 is connected to port 1240. In this configuration, the first loop 1242 is in fluid communication with the lumen 201 via the primary product stream 214, as well as the pressurized gas source 1208. The second loop 1244 is in fluid communication with the pump 1246 and the bulk product collection vessel 1216. If the reactor assembly 200 is operated, the pressurized gas source will pressurize the first loop 1242, and re-establishes the fluid communication between the primary product stream 214, and the lumen 201, and the primary product stream 214 will flow into the first loop 1242. If the pump 1246 is operated, the contents of the second loop 1244 will flow towards the bulk product collection vessel 1216 of the bulk product collection assembly 1205.

When the contents of the first loop reach port 1236, the valve may be moved to the second position, shown in FIG. 13. When in the second position, port 1226 is connected to port 1240, port 1228 is connected to port 1230, port 1232 is connected to port 1234, and port 1236 is connected to port 1238. In this configuration, the first loop 1242 is in fluid communication with the pump 1246 and the bulk product collection vessel 1216, and the second loop 1244 is in fluid communication with the lumen 201 via the primary product stream 214, as well as the pressurized gas source 1208. If the reactor assembly 200 continues to operate, the pressurized gas source 1208 will pressurize the second loop 1244 and the lumen 201, and the primary product stream 214 will flow into the second loop 1244. If the pump 1246 continues to operate, the contents of the first loop 1242, which was filled with product from the primary product stream 214 when the valve 1224 was previously in the first position, will be pumped towards bulk product collection vessel 1216.

As can be seen in FIGS. 12 and 13, by repeatedly actuating the valve 1224 between the first position and the second position, the first loop 1242 and second loop 1244 are alternately pressurized, and the primary product stream 214 is alternately directed to the one of the first loop 1242 and the second loop 1244 that is pressurized. Further, when not pressurized, the first loop 1242 and second loop 1244 are connected to the pump 1246, so that their contents are directed to the bulk product collection vessel 1216. By operating the product collection assembly in this manner, the primary product collection assembly 1202 may continuously receive and pressurize the primary product stream 214 from the reactor assembly 200, and continuously dispense a bulk product at atmospheric pressure to the bulk product collection assembly 1205, while the pressure in the lumen 201 is maintained.

In some examples, the actuation of the valve 1224 may be automatically controlled, for example by a computer, and the timing of the actuation may be determined by the computer based on the size of the loop.

In the particular example shown in FIGS. 12 and 13, the primary product collection assembly does not include a primary product collection vessel.

In the example of FIGS. 12 and 13, the first loop and second loop are external to the body of the valve 1224, and may be variable in size. In alternate examples, the first loop and second loop may be internal to the body of the valve 1224.

Optionally, as indicated by the use of dashed lines in FIGS. 12 and 13, while the system is in use some or all of the solvent or any other suitable inert fluid used by the pump 1246 to drive product out of the product filling loop 1244 in FIG. 12 or loop 1242 in FIG. 13 and into vessel 1216 can be temporarily accumulated and/or held in a portion of the pressurized gas source 1208. Optionally, the accumulated fluid can be intermittently or continuously withdrawn from the pressurized gas source 1208. Optionally, the solvent collected in the pressurized gas source 1246 may be removed from the system and discarded, or alternatively at least a portion of the accumulated fluid may be recycled back into the system. The recycled fluid may be reintroduced in to the system at any suitable location and/or using any suitable means.

In the example illustrated, the pressurized gas source 1208 is in fluid communication with a multistage pressure controlling device 1211 via an exit line 1219. Device pressure controlling device 1211 is capable of accepting and momentarily isolating the inert liquid from 1208 before draining the liquid into a collection vessel 1221. This may help facilitate removal of fluid from the system without causing significant depressurization of the system. The collection vessel 1211 can also help facilitate this process with the aid of any suitable back-pressure generating barrier. Alternatively, or in addition to removing some of the fluid via exit line 1219, at least a portion of the accumulated solvent can be reintroduced to the system, for example via a recycling line 1217 which is connected to the pump 1246 (either upstream or downstream from the pump 1246) stream either manually or through valves. In the illustrated example, the system includes an optional recycle stream carried in recycle line 1217 (shown using dashed lines) that is configured to facilitate unidirectional flow. This may help prevent fluid from flowing from the pump 1246 to the pressurized gas source 1208 via the recycle line 1217. To facilitate unidirectional flow the system may be provided with any suitable flow regulating apparatus, including, for example, a check valve 1213.

In any of the examples described above, various additional valves can be included in various positions in the assembly. For example, one or more additional valves may be positioned in the primary product stream or in the bulk product stream for diverting a second sample of the product to the sample collection assembly, or for diverting a portion of the product to waste.

While the above description provides examples of one or more processes or apparatuses, it will be appreciated that other processes or apparatuses may be within the scope of the accompanying claims.

The invention claimed is:

1. A fluid processing assembly comprising:
   a) a lumen for receiving at least one inlet stream and dispensing a primary product stream;
   b) an energizing device for supplying energy to an energizable portion of the lumen;
   c) a primary product collection assembly in fluid communication with the lumen for receiving the primary product stream, the energizable portion positioned exterior to the primary product collection assembly;
   d) a pressurized gas source downstream of the lumen, the pressurized gas source supplying pressurized gas to the primary product collection assembly for pressurizing at least a portion of the primary product collection assembly and the lumen; and
   e) a sample valve downstream of the lumen and upstream of the primary product collection assembly, the sample valve movable to divert a sample of the primary product stream.

2. The fluid processing assembly of claim 1, further comprising a tube, the tube forming the lumen.

3. The fluid processing assembly of claim 1, wherein the energizing device comprises an irradiating device irradiating an irradiation zone, the energizable portion within the irradiation zone.

4. The fluid processing assembly of claim 3, wherein the irradiating device comprises a microwave irradiating device.

5. The fluid processing assembly of claim 4, wherein the primary product collection assembly comprises a product collection vessel that is non-transparent to microwaves.

6. The fluid processing assembly of claim 4, further comprising a tube forming the lumen, wherein the tube is formed from a material that is transparent to microwaves.

7. The fluid processing assembly of claim 4, further comprising a tube forming the lumen, wherein the tube is formed from a material that absorbs microwaves.

8. The fluid processing assembly of claim 1, wherein the sample valve is configured to divert the sample without de-pressurizing the portion of the primary product collection assembly and the lumen.

9. The fluid processing assembly of claim 1, wherein the sample valve is a multi-port multi-position valve, the multi-port multi-position valve movable to direct the primary product stream from the lumen to the primary product collection assembly, isolate a plug from the primary product stream, and divert the plug to a sample stream.

10. The fluid processing assembly of claim 1, further comprising a bulk product collection assembly for receiving a bulk product from the primary product collection assembly, the bulk product assembly at atmospheric pressure, and the lumen remaining pressurized while the bulk product is dispensed to the bulk product collection assembly.

11. The fluid processing assembly of claim 10, wherein the primary product collection assembly comprises an outlet valve downstream of the lumen for receiving the primary product stream, the valve comprising a first loop and a second loop, the valve connected to the bulk product collection assembly and a pump.

12. The fluid processing assembly of claim 11, wherein:
   a) the outlet valve is movable between a first position and a second position; and
   b) when the outlet valve is in the first position, the first loop is in fluid communication with the lumen and the portion of the primary product collection assembly, and the second loop is in fluid communication with the pump and the bulk product collection assembly.

13. The fluid processing assembly of claim 12, wherein when the outlet valve is in the second position, the first loop is in communication with the pump and the bulk product collection assembly, and the second loop is in communication with the lumen and the portion of the primary product collection assembly.

14. The fluid processing assembly of claim 11, further comprising a recycle line fluidly connecting the portion of the primary product collection assembly and the pump to permit the flow of fluid from the pressurized gas source to the pump.

15. A method for processing fluids comprising:
   a) supplying a pressurized gas to a primary product collection assembly to pressurize at least a portion of the primary product collection assembly and a lumen upstream of the primary product collection assembly;
   b) flowing at least one inlet stream into the lumen;
   c) supplying energy to an energizable portion of the lumen, the energizable portion positioned exterior to the primary product collection assembly;
   d) dispensing a primary product stream from the lumen into the portion of the primary product collection assembly; and
   e) diverting a sample of the primary product stream while maintaining the pressure in the portion of the primary product collection assembly and in the lumen.

16. The method of claim 15, wherein step c) comprises irradiating the energizable portion with microwaves.

17. The method of claim 15, wherein step e) comprises moving a multi-port multi-position valve to isolate a plug from the primary product stream, and divert the plug to a sample stream.

18. The method of claim 15, further comprising f) continuously dispensing a bulk product from an outlet valve of the primary product collection assembly while maintaining the pressure in the lumen and the portion of the primary product collection assembly.

19. The method of claim 18, wherein step f) comprises alternately:
   i) connecting a first loop of an outlet valve of the primary product collection assembly in fluid communication with the lumen and in fluid communication with the portion of the primary product collection assembly; and
   ii) connecting a second loop of the outlet valve in fluid communication with the lumen and in fluid communication with the portion of the primary product collection assembly.

20. The method of claim 19, wherein step f) comprises alternately:
   i) dispensing the primary product stream from the lumen into the first loop of the outlet valve when the first loop is in fluid communication with the lumen; and
   ii) dispensing the primary product stream from the lumen into the second loop of the outlet valve when the second loop is in fluid communication with the lumen.

21. The method of claim 20, wherein step f) comprises alternately:
   i) connecting the first loop to a pump and to a bulk product collection assembly to dispense the contents of the first loop into the bulk product collection assembly; and
   ii) connecting the second loop to the pump and to the bulk product collection assembly to dispense the contents of the second loop into the bulk product collection assembly.

* * * * *